United States Patent
Plakogiannis et al.

(10) Patent No.: US 11,717,525 B2
(45) Date of Patent: *Aug. 8, 2023

(54) TRANSDERMAL AND/OR TOPICAL DELIVERY SYSTEM COMPRISING CLOBAZAM

(71) Applicant: Alpha to Omega Pharmaceutical Consultants, Inc., Whitestone, NY (US)

(72) Inventors: Fotios M. Plakogiannis, Whitestone, NY (US); Donald McAfee, Pt. Roberts, WA (US); Nisarg Modi, Jersey City, NJ (US)

(73) Assignee: Alpha To Omega Pharmaceutical Consultants, Inc., Whitestone, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/835,820

(22) Filed: Mar. 31, 2020

(65) Prior Publication Data

US 2020/0246353 A1 Aug. 6, 2020

Related U.S. Application Data

(63) Continuation of application No. 16/574,684, filed on Sep. 18, 2019, now Pat. No. 10,624,901, which is a continuation of application No. 15/221,673, filed on Jul. 28, 2016, now Pat. No. 10,449,201.

(60) Provisional application No. 62/205,909, filed on Aug. 17, 2015.

(51) Int. Cl.
*A61K 31/5513* (2006.01)
*A61K 9/70* (2006.01)
*A61K 31/551* (2006.01)
*A61P 25/08* (2006.01)
*A61P 25/22* (2006.01)

(52) U.S. Cl.
CPC ........ *A61K 31/5513* (2013.01); *A61K 9/7084* (2013.01); *A61K 31/551* (2013.01); *A61P 25/08* (2018.01); *A61P 25/22* (2018.01)

(58) Field of Classification Search
CPC .............. A61K 31/5513; A61K 9/7084; A61K 31/551; A61P 25/22; A61P 25/08
See application file for complete search history.

(56) References Cited

U.S. PATENT DOCUMENTS

| 5,225,198 A | 7/1993 | Sharma et al. |
| 5,552,153 A | 9/1996 | Behl |

OTHER PUBLICATIONS

Gauthier, A.C., et al., Clobazam: A safe, efficacious, and newly rediscovered therapeutic for epilepsy, CNS Neuroscience & Therapeutics, 21, 2015, pp. 543-548.

Remy, C., "Clobazam in the treatment of Epilepsy: A Review of the literature", Epilepsia 35(s5), Oct. 1994 (Oct. 1994), pp. S88-S91.

(Continued)

*Primary Examiner* — Kyung S Chang
(74) *Attorney, Agent, or Firm* — Joseph F. Murphy; Potomac Law Group, PLLC

(57) ABSTRACT

A Transdermal Drug Delivery System (TDDS) of the reservoir or plaster type for administrating clobazam for the treatment of various types of anxiety and epilepsy, for 1 day, 2 day, 3 day, 4 day, 5 day, 6 day and/or 7-day continuous application.

18 Claims, 4 Drawing Sheets

Clobazam Release from Liquid and gel formulation through human cadaver skin

(56) References Cited

OTHER PUBLICATIONS

Sharma, N., et al., "A Review: Transdermal drug delivery system: A tool for novel drug delivery system", International Journal of Drug Development & Research, 3(3), Jul.-Sep. 2011, pp. 70-84.

Ogiso, T., et al., "Membrance controlled transdermal therapeutic system containing clonazepam and anticonvulsant activity after its application", Chemical & Pharmaceutical Bulletin, 37(2), Feb. 1989 (Feb. 1989), pp. 446-449.

Soler, L.I., et al., "Transdermal delivery of alprazolam from a monolithic patch: formulation based on it vitro characterization", Drug Development and Industrial Pharmacy, 38(10), 2012 p. s1171-178.

International Search Report for PCT/ib2016/054578 dated Nov. 30, 2016.

Propylene Glycol Monolaurate Type I Safety Data Sheet. Sigma-Aldrich Inc. Print Date: Jun. 7, 2021.

Ropylene Glycol Monolaurate Type II Safety Data Sheet. Sigma-Aldrich Inc. Print Date: Jul. 6, 2021.

Fig.1 Clobazam Release from Liquid and gel formulation through human cadaver skin
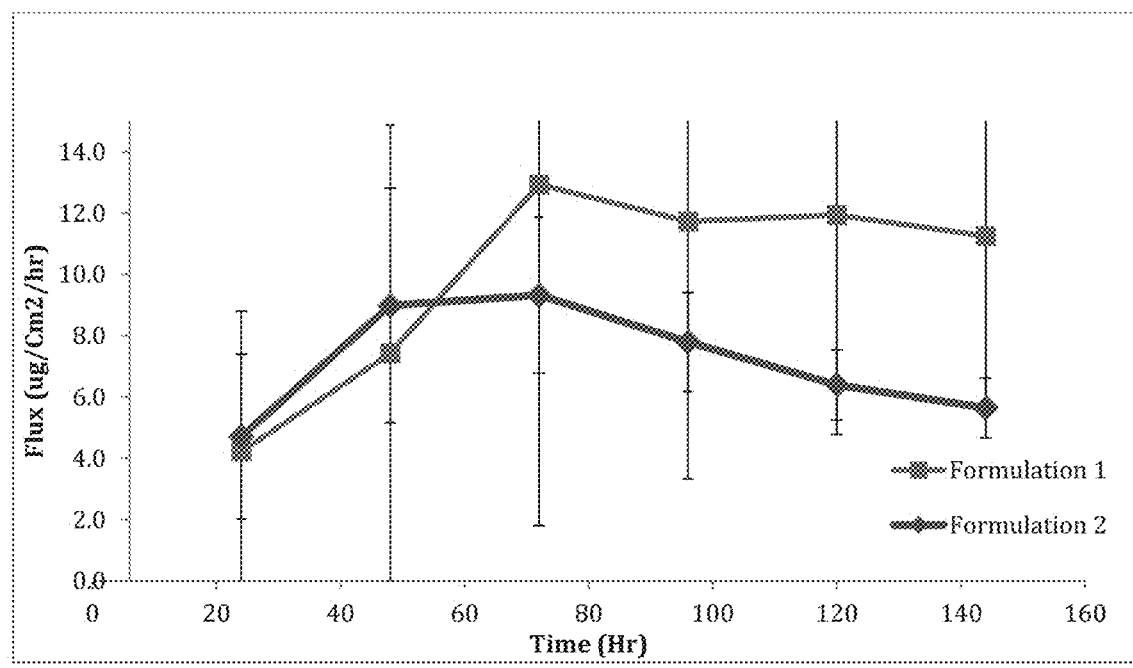

Fig.2 Effect of polymers on release of clobazam through Human cadaver skin
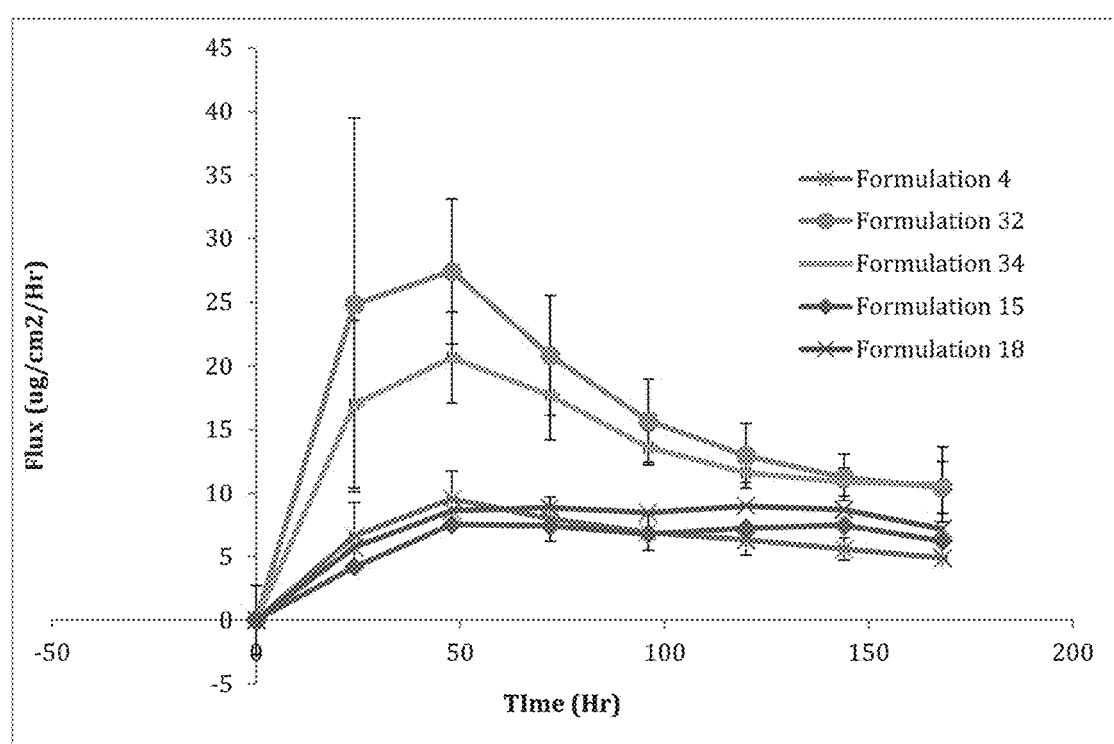

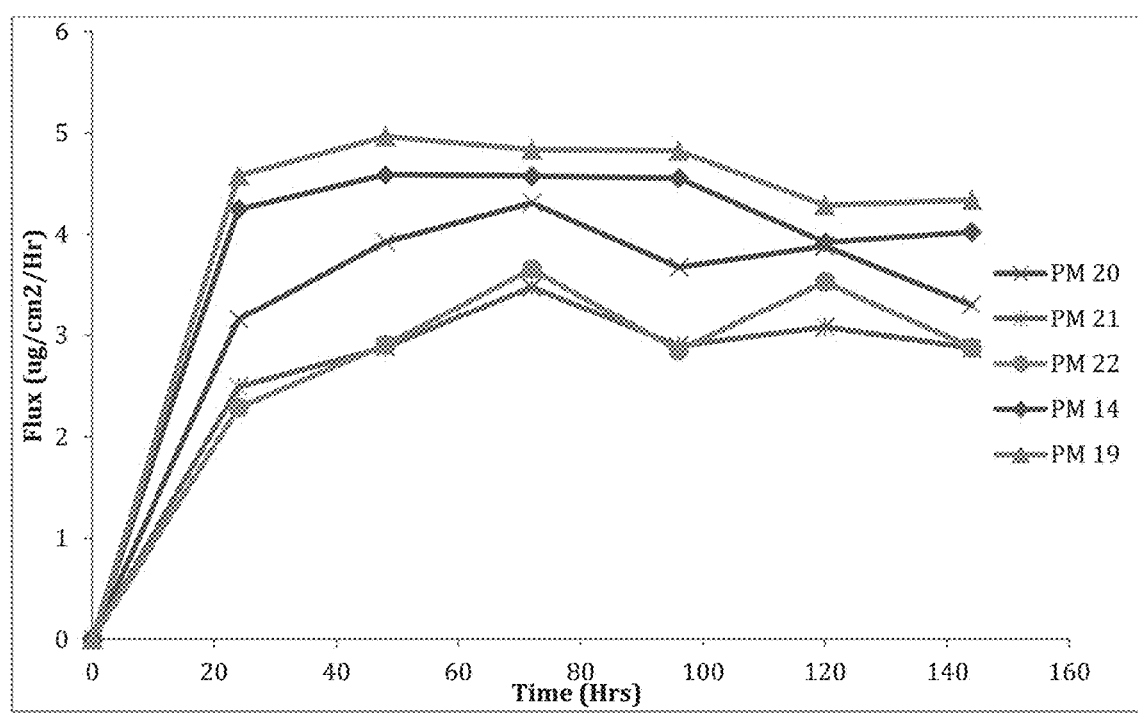
Fig.3 Clobazam release from TDDS matrix system through Human Cadaver Skin

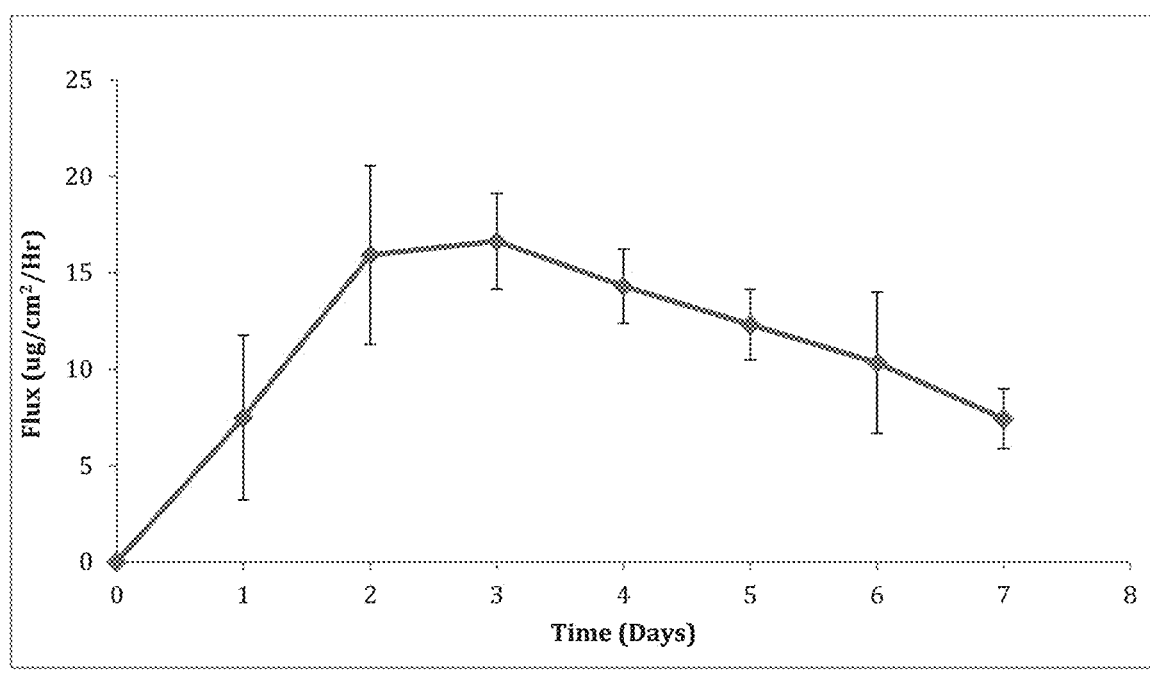
Fig.4 In-vitro diffusion from clobazam reservoir patch through human cadaver skin (Formulation 57)

TRANSDERMAL AND/OR TOPICAL DELIVERY SYSTEM COMPRISING CLOBAZAM

This application is a Continuation of U.S. Ser. No. 16/574,684 filed Sep. 18, 2019 which is a Continuation of U.S. Ser. No. 15/221,673 filed Jul. 28, 2016 and claims benefit under 35 U.S.C. § 119(e) of U.S. Provisional Patent Application No. 62/205,909, filed Aug. 17, 2015, the contents of which are incorporated in their entirety herein.

SPECIFICATION

Background of the Invention

The present invention relates to transdermal drug delivery system (TDDS) of pharmaceutical compositions, which have a satisfactory in-vitro performance and good bioavailability. In particular, the transdermal pharmaceutical composition of clobazam in the present invention includes either liquid or semi solid in a reservoir patch dosage form or matrix or adhesive in a plaster dosage form for treatment of certain types of epilepsy and anxiety for 1 Day, 2 Day, 3 Day, 4 Day, 5 Day, 6 Day and/or 7-day continuous application.

Epilepsy is a group of neurological disorders characterized by epileptic seizures. These epileptic seizures are the result of excessive and abnormal cortical nerve cell activity in the brain, which causes episodes that can vary from brief and nearly undetectable to long periods of vigorous shaking. Lennox-Gastaut syndrome (LGS) is a form of severe epilepsy that begins in childhood. Multiple types of seizures and intellectual disability characterize it. The prognosis for individual with LGS varies. There is no cure for the disorder. Complete recovery, including freedom from seizures and normal development, is very unusual.

Lennox Gastaut Syndrome is one of the catastrophic childhood epilepsy syndromes, which is characterized by multiple seizure types including but not limited to tonic, atonic, atypical absence and generalized tonic-clonic seizures.

LGS develops during first decade of life, typically between 3-5 years of age and is common in males. The basic symptoms of it are multiple types of generalized seizures, difficult to control and/or slowness of intellectual growth such as mental retardation and behavioral problems.

The prevalence of LGS in developed countries was approximately 2 per 100,000 children and in Europe 0.1-0.28 per 1000. Studies demonstrated that the figure of LGS is relatively consistent across the developed populations. In Atlanta, USA, LGS accounts for 4% of patients with childhood epilepsy, with a reported incidence of 0.26 per 1000 live birth. (1)

Clobazam is a newer 1,5-benzodiazepine that is better tolerated and effective for all seizure types including drop attack for LGS. Clobazam is a benzodiazepine, which acts to enhance the actions of inhibitory neurons in the brain. This is accomplished by binding to certain sites on neuronal GABA-A1 receptors in a manner that enhances their efficacy. Since GABA is the principle inhibitory neurotransmitter in the brain, the actions of benzodiazepines are to reduce neuronal activity, reduce anxiety, promote sedation, and prevent the uncontrolled spread of neural excitation that result in epileptic seizures. Clobazam is class IV controlled substance because benzodiazepines can induce drug dependence.

Clobazam, has the structure

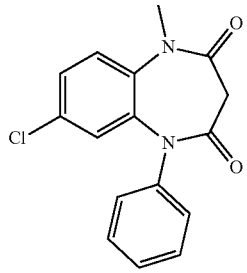 [SMILES: CN1C(=O)CC(=O)N(c2ccccc2)c2cc(Cl)ccc21]

It is practically insoluble in water at 25° C., with solubility of 70 microgram/ml (µg/ml). Clobazam is used to treat CNS related disorders such as anxiety and epilepsy. The drug is currently sold as suspension and tablet form for oral administration.

Clobazam, in particular, has some disadvantages, which result from pharmacokinetic parameters when administered orally. Clobazam is subject first-pass liver metabolism. Due to this first-pass metabolism, clobazam causes gastro-intestinal side effects such as constipation, vomiting, problem swallowing, and change of appetite. To maintain a therapeutically effective plasma level, the patient has to take orally 5 mg or 10 mg dose everyday based on their body weight. Moreover, the highest dose of clobazam is 20 mg or 40 mg on the basis of patient body weight, which is divided in two or three times a day. In addition, it is very difficult to give medicine to the children orally, sometimes crushing of tablet(s) produce large particles due to untrained individuals, which may increase risk of aspiration or chocking. (3). Furthermore, by taking clobazam orally during school hours and/or social activities, children can be stigmatizing by other children, which adversely affect to their psychology behavior such as aggression, depression and insomnia. Clobazam can also produce infections such as upper respiratory tract infection, pneumonia, and bronchitis. Poor patient compliance with oral LGS has been reported.

As such, there exists a need for composition and methods of delivering antiepileptic drugs, such as clobazam, to improve patient compliance and maximize the pharmacological profile of the active agent. This need is met by the invention of a transdermal drug delivery system (TDDS) for systemic delivery of clobazam in a patch form. This system is able to deliver sufficient amounts of clobazam in vivo for therapeutic effects.

Clobazam is only 87% absorbed when taken orally. Clobazam is extensively metabolized by the liver through N-demethylation and Hydroxylation process. According to the invention, the TDDS releases clobazam onto the patient's skin, from a novel formulation that promotes the diffusion of clobazam through the skin so that it becomes systemically available. The rapid metabolism caused by the first pass effect during oral administration is avoided. In addition, the TDDS, according to this invention ensures a constant delivery of the clobazam during an application period up to 7 days. In this way, the steady state plasma concentration can be maintained at a therapeutic level with a low frequency application. Delivering constant amount of clobazam through TDDS can compensate the short half-life of the clobazam. Furthermore, due to the transdermal administration, problems such as e.g. gastrointestinal intolerance, low enteral absorption or low per oral availability are eluded.

All references cited herein are incorporated herein by reference in their entireties.

BRIEF SUMMARY OF THE INVENTION

The structure of reservoir TDDS according to invention comprises an active substance, clobazam in the form of liquid, or semisolid or suspension in the pouch system. The pouch system contains impermeable backing layer, which covers the TDDS on the side averted from the skin and detachable protective layer containing release liner in contact with skin for controlled delivery of clobazam through the transdermal route.

The structure of matrix or plaster TDDS according to invention comprises an active substance, clobazam, suspended or solubilize in the polymer or adhesive matrix, cover between impermeable backing layer and release liner and/or detachable protective layer. According to current invention, the active substance, clobazam itself is solubilized or suspended in the pressure-sensitive adhesive or polymer matrix, or an extra placebo pressure sensitive adhesive layer may be provided which enables fixation of the TDDS on the skin.

The detachable and protective layer during storage covers the release liner in reservoir TDDS and the pressure sensitive adhesive TDDS surface facing the skin and is detached before application.

The invention comprises both TDDS designed as matrix system and or TDDS designed as reservoir membrane system.

The TDDS according to invention can be used both in the form of reservoir system as well as in the form of matrix system. According to this invention reservoir system comprises a pouch formed from an impermeable backing, a rate controlling membrane, an adhesive peripheral ring, covered by a strippable protective backing. The impermeable backing is configured to provide a central volume, which contains a drug reservoir in the form of a semisolid or liquid having dissolved and suspended drug, therein. Although preferred embodiments of this invention utilize an adhesive peripheral ring outside the path of drug from the system to the skin but other means for maintaining the system on the skin can be employed. Such means include an in-line adhesive layer; adhesive overlays or other fastening means such as buckles, belts and elastic armbands is also contemplated.

The TDDS according to invention can be manufactured in such a manner that this active substance, clobazam containing mixture is coated onto a suitable support, for example to a thermoplastic film provided with a silicone layer, and possibly after evaporation of the solvent components-is covered with a further film which will later constitute the backing layer of TDDS. The pharmaceutically acceptable substance suitable as auxiliaries such as plasticizer, tackifiers, solubilizers, stabilizers, fillers, carrier substances and permeation enhancers are in principle known to these skilled in the art.

The device of the present invention can release drug continuously by diffusion process. In this mode, the driving force is the difference in clobazam activity between the device reservoir and the skin and underlying tissue. The clobazam, which is entirely dissolved or disperse in the carrier and/or vehicle and/or polymer system in the case of present invention, permeates through the carrier to the skin. The reservoir or matrix system is in diffusion communication with the skin—which means that it either contacts the skin directly or contacts semipermeable material interposed between the reservoir or matrix system and the skin that provide permeation pathway for the clobazam and permeation enhancer to migrate from the reservoir or matrix to the skin. The interposed material may be homogenous, heterogeneous, or be composed of multiplicity of distinct layer.

Suitable base polymers for producing the active substance reservoir or matrix or the pressure sensitive adhesive layer of the TDDS according to invention are polymers based on cellulose and its derivatives (methylcellulose, ethyl cellulose, carboxymethyl cellulose, Hydroxypropyl cellulose, hydroxypropylmethyl cellulose etc.), natural polymers, polysaccharides and its derivatives such as but not limited to (agar, alginic acid and derivatives, cassia tora gum, collagen, gelatin, gellan gum, guar gum, pectin, potassium or sodium carrageenan, tragacanth, xanthan gum, copal, starch, chitosan, resin etc.), synthetic polymers and its derivatives such as without any limitation to carboxy vinyl polymers or carbomers (carbopol 940, carbopol 934, carbopol 971), polyethylene and its co-polymers etc. clays such as silicate etc. polyvinyl alcohol, polyacrylamide, polyvinyl pyrrolidone homopolymer and polyvinyl pyrrolidone copolymers (PVP, Poloxamer), acrylic acid its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, as well as pressure sensitive adhesive based on silicone, or "hot-melt adhesive". The term "hot-melt adhesive" comprises any adhesive which are not liquefied with solvent but by melting at elevated temperature, preferably in the range of from 60-200° C. Suitable as hot-melt adhesive are in particular, mixture of esters of hydrogenated colophony with cellulose derivatives. The mentioned base polymers may also be used in form of suitable mixtures.

On top of the above-mentioned polymers other polymers known to the skilled artisan may also be used as a base polymer for producing polymer vehicle or the matrix or the pressure sensitive adhesive layer, provided they are compatible with clobazam. In theory, a variety of polymers, resins and additives known to the art can be taken into consideration for production of TDDS. However, care must be take that these substances, in so far as coming into contact with the skin, are tolerated by the skin, and that the formulation is suitable for delivering clobazam.

In another embodiment, the active substance, clobazam is in the simplest case dispersed, coarsely, colloidally or molecularly, in a solution or melt of base polymers. In the further TDDS manufacturing techniques, the clobazam is in the form of supersaturated solution, nano-emulsion or nano-suspension, amorphous, crystalline, co-crystals, coated with base polymers or solubilize in polymers using hot melt extrusion process.

A preferred embodiment of the invention consists in that the active substance clobazam is present in the reservoir of TDDS in dissolved condition; in this case the formulation should, if possible, contain a solubilizer. Selected examples for solubilizers are polysorbate such as but not limited to (polysorbate 20, polysorbate 40, polysorbate 60, polysorbate 80 etc.), span such as but not limited to (span 80, span 20 etc.), surfactants such as (anionic, cationic, nonionic and amphoteric), propylene glycol monocaprylate type I, propylene glycol monocaprylate type II, propylene glycol dicaprylate, medium chain triglycerides, propylene glycol monolaurate type II, linoleoyl polyoxyl-6 glycerides, Caprylic glyceride, oleoyl-polyoxyl-6-glycerides, lauroyl polyoxyl-6-glycerides, polyglyceryl-3-dioleate, diethylene glycol monoethyl ether, propylene glycol monolaurate type I etc., cyclodextrins, polyhydric alcohol, especially 1,2-propanediol, butanediol, glycerine, polyethylene glycol (m.w. 200 and higher), Dimethyl Sulfoxide, Dimethyl Isosorbide, tetrahydrofurfuryl alcohol, diethyl tolumide, monoisopropylidene glycerine and others Solubilizers, surfactants, emulsifying agents, dispersing agents and similar compounds or chemicals known to those skilled in the art can be used either alone or in combination thereof. It has proved to be advantageous for the portion of the solubilizer to be 1 to 99% wt., especially preferred 5 to 75% wt. relative to the overall weight of the clobazam reservoir. It is to be taken into consideration that some of the mentioned solubilizers, e.g. Dimethyl Sulfoxide, Dimethyl Isosorbide, diethylene glycol monoethyl ether, can simultaneously act as a permeation enhancing agents.

In another embodiment, solvents can be also used to make up the weight of the total reservoir or matrix or pressure sensitive adhesive matrix systems. Theses solvents can also be used to increase the solubility of clobazam in the reservoir or matrix systems. Such solvents known to those skilled in the art can be used either alone or in mixture thereof without any limitation to following like alcohol $C_1$-$C_{20}$ such as but not limited to (methanol, ethanol, isopropyl alcohol, butanol, propanol etc.), polyhydric alcohols, isopropyl myristate, water, glycols such as but not limited (propylene glycol, polyethylene glycol, dipropylene glycol, hexylene glycol, glycerine etc.), pyrrolidone such as but not limited to (N-methyl 2-pyrrolidone, 2-pyrrolidone etc.), sulfoxides such as but not limited to (dimethyl Sulfoxide, decyl methyl sulfoxide etc.), dimethyl Isosorbide, mineral oils, vegetable oils, volatile chemicals which can be used to make matrix patch such as but not limited to (ethanol, propanol, ethyl acetate, acetone, methanol, dichloromethane, chloroform, toluene, Isopropyl alcohol), acids such as but not limited to lactic acid, acetic acid, bases and others.

To achieve a high clobazam flux through the skin, it has proved particularly beneficial, especially in matrix or adhesive systems, for the clobazam reservoir or matrix or pressure sensitive adhesive to contain permeation enhancing excipients in an amount of 0.1 to 25% wt, preferably from 1 to 15% wt, in each case relative to the total weight of the clobazam reservoir or matrix or pressure sensitive adhesive. Preferred example for skin permeation-enhancing agents are water, sulfoxides, and similar chemicals such as but not limited to (dimethyl sulfoxide, dimethyl acetamide, dimethylformamide, decyl methyl sulfoxide, dimethyl Isosorbide etc.), azone, pyrrolidones such as but not limited to (N-methyl-2-pyrrolidone, 2-pyrrolidon etc.), esters such as but not limited to (Propylene glycol monolaurate, butyl ethanoate, ethyl ethanoate, isopropyl myristate, isopropyl palmitate, methyl ethanoate, decyl oleate, glycerol monooleate, glycerol monolaurate, lauryl laurate etc.), fatty acids such as but not limited to (capric acid, caprylic acid, lauric acid, oleic acid, myristic acid, linoleic acid, stearic acid, palmitic acid etc.), alcohols, fatty alcohols and glycols such as but not limited to (oleyl alcohol, ethanol, dodecanol, propylene glycol, glycerol etc.), ethers such as but not limited to (diethylene glycol monoethyl ether), urea, polyoxyethylene fatty alcohol ethers, polyoxyethylene fatty acid esters, esters of fatty alcohols, esters of long chain fatty acids with methyl, ethyl or isopropyl alcohol, esters of fatty alcohols with acetic acid, lactic acid, as well as oleic acid diethanolamine, essential oils, terpene and terpenoids such as but not limited to (terpineol, limonene, thymol, cineole etc.), surfactant type enhancers (polysorbate 80, polysorbate 20 etc.), liposomes, niosomes, transferomes, ethanosomes, etc. and all penetration or permeation enhancers referred in the book "Percutaneous Penetration Enhancers" (Eric W. Smith, Howard I. Mailbach, 2005. Nov., CRC press). The permeation-enhancing substances mentioned above may be added either singly or as a mixture.

To achieve maximum release at constant release rate, the clobazam concentration in the active substance matrix or reservoir or pressure sensitive adhesive is preferably as optimized as possible. In this content, it has to be kept in mind, however, that the physical stability of the active substance may be adversely affected if the concentration is too high due to super-saturation, which causes precipitation. In the current invention of TDDS, the clobazam concentrations employed are in the range 0.1 to 50%-wt, in particular from 1 to 25% wt, in each case relative to the total weight of the active substance reservoir or matrix or pressure sensitive adhesives.

Moreover, the clobazam matrix or pressure sensitive adhesive or individual layers of the matrix may contain plasticizers which are known to those skilled in the art either alone or in combination thereof without any limitation to following like glycerol and its esters, phosphate esters, glycol derivatives, sugar alcohols, sebacic acid esters, azelate, citric acid esters, tartaric acid esters, adipate, phthalic acid esters, triacetin, oleic acid esters and all the plasticizers which can be used in transdermal drug delivery system referred in the book "Handbook of Plasticizers" (George Wypych, 2004, Chem Tec Publishing). The concentration of these plasticizers may be up to 50% wt, and is preferably between 5 to 25% wt, in each case relative to the active substance matrix total weight.

The invention also comprise such embodiments where the clobazam matrix has a two or multi-layered structure, also called multi-laminate drug in adhesive patch. For example, the various matrix layers may contain polymer constitutes from the above-mentioned polymers. In this case, the matrix layers are differing from each other's in the term of polymer or pressure sensitive or hot melt polymers composition, clobazam concentration, different permeating enhancers or solubilizers. The layers can be separated using semi-permeable membrane between two distinct drug-in-adhesive layers or multiple drug-in-adhesive layers under a single backing film.

The invention provides a transdermal drug delivery system (TDDS) for administration of clobazam comprising: an active substance area or reservoir comprises a pharmaceutical composition comprising clobazam and at least one excipient; an impermeable backing layer;
optionally, a releasing membrane, which is covered by a detachable backing layer. The invention provides a TDDS wherein the active substance area or reservoir is configured as a polymer matrix system, a liquid system, a gel system, or a pressure sensitive adhesive system.
The invention provides a TDDS, wherein the active substance reservoir is constructed in a pouch-shaped system. The invention provides a TDDS, wherein the active substance reservoir is a preparation selected from the group consisting of flowable, viscous, semi-solid, gel-like, liquid preparation, solution, suspension, and emulsion. The invention provides a TDDS wherein the active substance reservoir is confined on the skin facing side by an active substance permeable membrane and on the opposite side from the skin by an active substance impermeable layer.
The invention provides a TDDS comprising an active substance permeable membrane which modifies or controls the rate of active substance release. The invention provides a TDDS characterized in that the clobazam containing area is a single-, double-, or multilayered active substance matrix.

The invention provides a TDDS further comprising an adhesive so that it may be applied as a plaster or bandage. The invention provides a TDDS wherein the active substance is a matrix selected from the group consisting of a plastic or synthetic resin matrix, a pressure-sensitive adhesive matrix, wherein the basic polymer(s) of this matrix are selected from the group consisting of polymers based on acrylic acid and its esters, isobutylenes, ethylene-vinyl acetate copolymers, natural rubbers, synthetic rubbers, styrene-diene copolymers, styrene-butadiene block copolymers, isoprene block copolymers, acrylonitrile-butadiene rubber, butyl rubber and neoprene rubber, pressure sensitive adhesives based on silicone, hot-melt adhesive, mixtures of esters of hydrogenated colophony with cellulose derivatives, and combinations thereof. The invention provides a TDDS wherein the active substance reservoir contains a fiber material, a woven fabric or a nonwoven, to which the active substance is adsorbed. The invention provides a TDDS can deliver 1-40 mg/day clobazam through the skin to the blood in a subject, which can produce up to 2000 ng/ml plasma concentration. The invention provides a TDDS wherein the clobazam is present in a concentration in the range of from 0.1-50 wt %, preferably from 1-30 wt %, more preferably 1-20 wt %, in each case relative total mass of the active substance reservoir.

The invention provides a TDDS wherein clobazam is present in the active substance reservoir either in dissolved or suspended state. The invention provides a TDDS wherein the active substance reservoir contains at least one solubilizer, preferably in an amount of from 1 to 99 wt %, with particular preference from 5 to 70 wt %, in each case relative to the total weight of the active substance reservoir. The invention provides a TDDS wherein the solubilizer is selected from the group consisting of polysorbate, span, surfactants (anionic, cationic, nonionic and amphoteric), propylene glycol monocaprylate and its derivatives, glycols and its derivatives, triglycerides and its derivatives, diethylene glycol monoethyl ether, cyclodextrins, polyhydric alcohol, polyethylene glycol (m.w. 200 and higher), tetrahydrofurfuryl alcohol, diethyl tolumide, monoisopropylidene glycerine, sulfoxides, and similar chemicals such as but not limited to dimethyl sulfoxide, dimethyl acetamide, dimethyl formamide, decyl methyl sulfoxide, dimethyl isosorbide, Caprylocaproyl polyoxyl-8 glycerides, triacetine, and combinations thereof.

The invention provides a TDDS wherein the active substance reservoir contains at least one permeation-enhancing agent, in an amount of from 0.1 to 50 wt %, with particular reference from 1 to 25 wt %, in each case relative to the total weight of the active substance reservoir. The invention provides a TDDS where in the permeation-enhancing agent is selected from the group consisting of azone, pyrrolidones, N-methyl-2-pyrrolidone, 2-pyrrolidone, esters, Propylene glycol monolaurate, butyl ethanoate, ethyl ethanoate, isopropyl myristate, isopropyl palmitate, methyl ethanoate, decyl oleate, glycerol monooleate, glycerol monolaurate, lauryl laurate, fatty acids, alcohols, fatty alcohols and glycols, ethers, urea, polyoxyethylene fatty alcohol ethers, polyoxyethylene fatty acid esters, esters of fatty alcohols, esters of long chain fatty acids with methyl, ethyl or isopropyl alcohol, esters of fatty alcohols, acetic acid, lactic acid, diethanolamine, essential oils, propylene glycol monolaurate type I and type II, terpene and terpenoids, surfactant type enhancers, and combinations thereof.

The invention provides a TDDS characterized in that during application period of the TDDS an irritation score should be minimum 0 and maximum 2. The invention provides a TDDS use of a clobazam-containing TDDS according to ay one of claims 1 to 13 for treating any of the various types of epilepsy including, but not limited to, complex partial, simple partial, status epilepticus, and non-status absence seizures.

The invention provides a method of treating and/or preventing epilepsy comprising:
  selecting a patient in need of such treatment and/or prevention; applying to the skin of the patient a TDDS of the invention; thereby treating and/or preventing the epilepsy. The invention provides a method of treating and/or preventing anxiety comprising: selecting a patient in need of such treatment and/or prevention; applying to the skin of the patient a TDDS of the invention thereby treating and/or preventing the anxiety. The invention provides a method wherein the anxiety is agitation, acute, chronic, or severe anxiety.

The invention provides a method of treating and/or preventing Lennox-Gastaut Syndrome (LGS) type of epilepsy comprising: selecting a patient in need of such treatment and/or prevention; applying to the skin of the patient a TDDS of the invention; thereby treating and/or preventing the LGS. The invention provides a method according characterized in that the application period of the TDDS is at least 24 hr and maximally 7 days.

The invention provides a method of making a transdermal drug delivery system (TDDS) for administration of clobazam comprising: providing an active substance area or reservoir; providing an impermeable backing layer; optionally providing a releasing membrane, which is covered by a detachable backing layer, wherein the active substance area or reservoir comprises a pharmaceutical composition comprising clobazam and at least one excipient.

The invention provides a method of treating and/or preventing epilepsy comprising the following steps: selecting a patient in need of such treatment and/or prevention; applying to the skin of the patient a transdermal drug delivery system (TDDS) comprising: an active substance area or reservoir comprising a pharmaceutical composition comprising about 4% to about 6% Clobazam; about 20% to about 25% diethylene glycol monoethyl ether; about 10% to about 12% triacetin; about 10% to about 25% of a surfactant selected from the group consisting of caprylocaproyl polyoxyl-8 glycerides, polyethylene glycol sorbitan monolaurate, propylene glycol monolaurate, and mixtures thereof; about 5% to about 6% Lactic Acid; about 10% to about 15% glycols; about 20% to about 35% mixture of dimethylsulfoxide and dimethylisosorbide; about 0.1% to about 5% gelling agent; about pH 5.0 to about 6.0, wherein the percentage of components are weight to weight of the composition, further wherein the TDDS comprises an impermeable backing layer and a releasing membrane, which is covered by a detachable protective layer, and further wherein the application period of the TDDS is 7 days, thereby treating and/or preventing epilepsy in the patient. The invention provides a method wherein the epilepsy is the Lennox-Gastaut Syndrome (LGS) type of epilepsy. The invention provides a method wherein the active substance area or reservoir is configured as a polymer matrix system, a liquid system, a gel system, or a pressure sensitive adhesive system. The invention provides a method wherein the active substance reservoir is constructed in a pouch-shaped system. The invention provides a method wherein the active substance reservoir is a preparation selected from the group consisting of flowable, viscous, semi-solid, gel-like, liquid preparation, solution, suspension, and emulsion. The invention provides a method wherein the active substance reservoir is confined on the skin facing side by an active substance permeable membrane and on the opposite side from the skin by an active substance impermeable layer. The invention provides a method comprising an active substance permeable membrane which modifies or controls the rate of active substance release. The invention provides a method characterized in that the clobazam containing area is a single-, double-, or multi-layered active substance matrix. The invention provides a method further comprising an adhesive so that it may be applied as a plaster or bandage. The invention provides a method wherein the active substance is in a matrix selected from the group consisting of a plastic or synthetic resin matrix, a pressure-sensitive adhesive matrix, wherein the basic polymer(s) of this matrix are selected from the group consisting of polymers based on acrylic acid and its esters, isobutylenes, ethylene-vinyl acetate copolymers, natural rubbers, synthetic rubbers, styrene-diene copolymers, styrene-butadiene block copolymers, isoprene block copolymers, acrylonitrile-butadiene rubber, butyl rubber and neoprene rubber, pressure sensitive adhesives based on silicone, acrylic, polyisobutylene, hot-melt adhesive, mixtures of esters of hydrogenated colophony with cellulose derivatives, and combinations thereof. The invention provides a method wherein the active substance reservoir contains a fiber material, a woven fabric or a nonwoven, to which the active substance is adsorbed. The invention provides a method wherein the TDDS delivers 1-40 mg/day clobazam through the skin to the blood in a subject, further wherein the TDDS produces up to 2000 ng/ml plasma concentration. The invention provides a method wherein clobazam is present in the active substance reservoir either in dissolved or suspended state. The invention provides a method wherein the composition weight is about 100 mg/cm2 to about 500 mg/cm2 of active surface area. The invention provides a method wherein the composition is a gel formulation wherein the glycol is hexylene glycol. The invention provides a method wherein the composition is a gel formulation wherein the gelling agent is hydroxypropyl cellulose.

The invention provides a clobazam-containing TDDS for use in the preparation of a medicament for use in treating and/or preventing epilepsy or treating and/or preventing Lennox-Gastaut Syndrome (LGS) type of epilepsy. A method for treating or preventing a disease or condition in a patient, wherein the disease or condition is selected from the group consisting of epilepsy and/or LGS epilepsy, and combinations thereof, wherein said method comprises: selecting a patient in need of treating or preventing said disease or condition; administering to the patient the composition of the invention in a therapeutically effective amount, thereby treating or preventing said disease in said patient.

BRIEF DESCRIPTION OF SEVERAL VIEWS OF THE DRAWINGS

The invention will be described in conjunction with the following drawings in which like reference numerals designate like elements and wherein:

FIG. 1: Clobazam release through human cadaver skin from liquid and gel formulations.

FIG. 2: Effect of different polymer on the release of clobazam through human cadaver skin.

FIG. 3: Release of clobazam from Transdermal adhesive formulation through human cadaver skin.

FIG. 4: In-vitro release study of clobazam from formulation 57 through human cadaver skin.

DETAILED DESCRIPTION OF THE INVENTION

Clobazam refers to all pharmaceutically acceptable forms of clobazam either alone or in combinations thereof, for example in following forms but not limited to such as free base or salt or isomer or amorphous or crystalline or co crystalline or solid solution or prodrug or analog or derivatives or metabolites.

LGS: Lennox-Gastaut syndrome
TDDS: Transdermal drug delivery system
TDS: Transdermal delivery system
Range:
 Terms transdermal and topical are used interchangeably.
 Terms Formulation and composition are used interchangeable.
 Terms Transdermal drug delivery system and transdermal delivery system are used Interchangeably.
 Terms reservoir system and reservoir patch are used interchangeably.
 Terms matrix system and matrix patch are used interchangeably.
 Terms transdermal composition and pharmaceutical composition are used interchangeably.
 Term liquid includes without any limitation solution, suspension, micro suspension, nano suspension, dispersion, sprays, aerosols, where solutions are preferred.
 The term semisolid includes without any limitation such as gels, ointments, creams, emulsion, microemulsion, nanoemulsion, paste, balms, magma, lotions, mousses, waxes, where gels are preferred.
 The term polymer film includes polymer without any limitation pressure sensitive adhesive and/or non-adhesive polymer.
 Transdermal delivery system: Reservoir system and/or matrix system comprising Pharmaceutical composition.
 All the pharmaceutical compositions are percent by weight.
 Without any limitation enhancers used in liquid formulation can be used for semi solid and polymer formulation.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "agent" refers to any molecule, compound, methodology and/or substance for use in the prevention, treatment, management and/or diagnosis of a disease or condition. As used herein, the term "effective amount" refers to the amount of a therapy that is sufficient to result in the prevention of the development, recurrence, or onset of a disease or condition, and one or more symptoms thereof, to enhance or improve the prophylactic effect(s) of another therapy, reduce the severity, the duration of a disease or condition, ameliorate one or more symptoms of a disease or condition, prevent the advancement of a disease or condition, cause regression of a disease or condition, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "therapeutic agent" refers to any molecule, compound, and/or substance that is used for the purpose of treating and/or managing a disease or disorder.

As used herein, the terms "therapies" and "therapy" can refer to any method(s), composition(s), and/or agent(s) that can be used in the prevention, treatment and/or management of a disease or condition, or one or more symptoms thereof. In certain embodiments, the terms "therapy" and "therapies" refer to small molecule therapy.

As used herein, the terms "treat," "treatment," and "treating" in the context of the administration of a therapy to a subject refer to the reduction or inhibition of the progression and/or duration of a disease or condition, the reduction or amelioration of the severity of a disease or condition, such as cancer, and/or the amelioration of one or more symptoms thereof resulting from the administration of one or more therapies.

The term "derivative" or "derivatized" as used herein includes chemical modification of a compound of the invention, or pharmaceutically acceptable salts thereof or mixtures thereof. That is, a "derivative" may be a functional equivalent of a compound of the invention, which is capable of inducing the improved pharmacological functional activity in a given subject. Illustrative of such chemical modifications would be replacement of hydrogen by a halo group, an alkyl group, an acyl group or an amino group.

As used herein, the term "pharmaceutically acceptable salts" includes acid addition salts or addition salts of free bases. The term "pharmaceutically acceptable salts" of a compound of the invention is also meant to include within its scope all the possible isomers and their mixtures, and any pharmaceutically acceptable metabolite, bioprecursor and/or pro-drug, such as, for example, a compound which has a structural formula different from the one of the compounds of the invention, and yet is directly or indirectly converted in vivo into a compound of the invention, upon administration to a subject, such as a mammal, particularly a human being.

The compound may be in the form of a pharmaceutically acceptable salt, such as an acid addition salt or a base salt, or a solvate thereof, including a hydrate thereof. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminium, calcium, magnesium, zinc and diethanolamine salts.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "transdermal" refers to delivery, administration or application of a drug by means of direct contact with skin or mucosa. Such delivery, administration or application is also known as dermal, percutaneous, transmucosal and buccal. As used herein, "dermal" includes skin and mucosa, which includes oral, buccal, nasal, rectal and vaginal mucosa.

As used herein, "transdermal drug delivery system" refers to a system (e.g., a device) comprising a composition that releases drug upon application to the skin (or any other surface noted above). A transdermal drug delivery system may comprise a drug-containing composition, and, optionally, a backing layer and/or a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. Typically, transdermal drug delivery systems are classified into one of two categories: matrix-type systems and reservoir-type systems, as discussed in more detail below.

A transdermal drug delivery system also may include a drug impermeable backing layer or film. In some embodiments, the backing layer is adjacent the drug-containing composition. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. For example, 3M's Scotch Pak® 1012 or 9732 (a polyester film with an ethylene vinyl acetate copolymer heat seal layer), 9723 (a laminate of polyethylene and polyester), or CoTran 9720 (a polyethylene film) are useful in the transdermal drug delivery systems described herein, as are Dow® backing layer films, such as Dow® BLF 2050 (a multi-layer backing comprising ethylene vinyl acetate layers and an internal SARAN® layer.

A transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated Bio-Release® liner and Syl-off® 7610, Loparex's PET release liner (silicone-coated) and 3M's 1020, 1022, 9741, 9744, 9748, 9749 and 9755 Scotchpak.™. (fluoropolymer-coated polyester films).

A transdermal drug delivery system may be packaged or provided in a package, such as a pouchstock material used in the prior art for transdermal drug delivery systems in general. For example, DuPont's Surlyn® can be used in a pouchstock material. Alternatively, a pouchstock comprising a coextruded ethylene acrylic acid/low-density polyethylene (EAA/LDPE) material, or Barex® from INEOS (acrylonitrile-methyl acrylate) may be used.

The invention provides pharmaceutical composition for transdermal delivery of clobazam up to 7 days.

In one embodiment, the invention provides pharmaceutical compositions as liquid formulation for transdermal delivery of clobazam. In one aspect the invention further provides liquid formulation comprising clobazam and vehicle system. The invention further provides the vehicle system, which comprises solvents (solubilizer), permeation enhancing agents, if required acid or base for pH adjustment mentioned should be use. The liquid formulation comprising clobazam and vehicle system is preferred.

In one aspect liquid formulation comprise clobazam and vehicle system wherein, Clobazam is present in an amount between 0.1-50 wt %, vehicle system is present in an amount between 5-99.9 wt %. More preferably, Clobazam is present in an amount between 1-25 wt %, vehicle system is present in an amount between 1-99 wt %. The invention further provides an exemplary composition of the invention comprising about 0.1-50 wt % clobazam, 0.1-99.9 wt % dimethylsulfoxide, 0.1-99.9 wt % dimethylisosorbide, 0.1-99.9 wt % dipropylene glycol, 0.1-99.9 wt % highly purified diethylene glycol monoethyl ether, 0.1-50 wt % fatty acid, 0.1-50 wt % Lactic acid, 0.1-99.9% wt propylene glycol, 0.1-99.9% wt polyethylene glycol-400, 0.1-50% wt water, pH between 3.5-8. More Preferably, about 1-25 wt % clobazam, 5-50 wt % dimethylsulfoxide, 5-50 wt % dimethylisosorbide, 1-25 wt % dipropylene glycol, 1-50 wt % highly purified diethylene glycol monoethyl ether, 0.1-20 wt %, fatty acid, 0.1-20 wt % Lactic acid, 1-25% wt propylene glycol, 1-25% wt polyethylene glycol-400, 1-25% wt water, pH adjusted between 4-7. Without limiting in scope an exemplary formulation in this range is illustrated in Example 1.

In another embodiment, the invention provides pharmaceutical compositions as semisolid formulation for transdermal delivery of clobazam for up to 7 days.

In one aspect the invention further provides semisolid formulation comprising clobazam and polymeric vehicle system. The invention further provides the vehicle system, which comprise solvents (Solubilizer), permeability enhancing excipients and polymer or gelling agent or thickening agent, if required acid or base for pH adjustment. The semisolid formulation comprising clobazam and a polymeric vehicle system is preferred.

One aspect of semisolid formulation comprises clobazam and a polymeric vehicle system wherein, clobazam is present in an amount between 0.1-50 wt %, and the polymeric vehicle system is present in an amount between 0.1-99.9 wt %. More preferably, clobazam is present in an amount between 1-30 wt %, and the polymeric vehicle system is present in an amount between 25-99 wt % to make up to 100 wt %.

The invention further provides an exemplary formulation of the invention comprising about 0.1-50 wt % clobazam, 0.5-99.9 wt % dimethylsulfoxide, 0.5-99.9 wt % polyethylene glycol-400, 0.5-99.9 wt % diethylene glycol monoethyl ether, 0.5-99.9% wt propylene glycol, 0.5-99.9 wt % dipropylene glycol, 0.1-50 wt % Lactic acid, 0.5-99.9 wt %, dimethyl isosorbide, 0.5-50 wt % fatty acid, 0.5-50% wt water, 0.1-50% wt polyvinyl pyrrolidone, pH between 3.5-8. More Preferably, about 1-25 wt % clobazam, 0.5-50 wt % dimethylsulfoxide, 0.5-50 wt % polyethylene glycol-400, 0.5-50 wt % diethylene glycol monoethyl ether, 0.5-50% wt propylene glycol, 0.5-50 wt % dipropylene glycol, 0.1-20 wt % Lactic acid, 0.5-50 wt %, dimethyl isosorbide, 0.5-50 wt % fatty acid, 0.5-50% wt water, 0.1-30% wt polyvinyl pyrrolidone, pH adjusted between 4-7.

The invention further provides another exemplary formulation of the invention comprising about 0.1-25 wt % clobazam, 0.5-50 wt % dimethylsulfoxide, 0.5-50 wt % polyethylene glycol-400, 0.5-50 wt % highly purified diethylene glycol monoethyl ether, 0.5-50% wt propylene glycol, 0.5-50 wt % dipropylene glycol, 0.1-20 wt % Lactic acid, 0.5-50 wt %, dimethyl isosorbide, 0.5-50 wt % fatty acid, 0.5-50% wt water, 0.1-30% wt polyvinyl pyrrolidone, 0.1-15 wt % hydroxypropyl cellulose HF, pH adjusted between 4-7.

The invention further provides yet another exemplary formulation of the invention comprising about 0.1-25 wt % clobazam, 0.5-50 wt % dimethylsulfoxide, 0.5-50 wt % polyethylene glycol-400, 0.5-50 wt % highly purified diethylene glycol monoethyl ether, 0.5-50% wt propylene glycol, 0.5-50 wt % dipropylene glycol, 0.1-20 wt % Lactic acid, 0.5-50 wt %, dimethyl isosorbide, 0.5-30 wt % Caprylocaproyl polyoxyl-8 glycerides, 0.5-50 wt % Propylene glycol monolaurate type II, 0.5-30% wt Tween-20, 0.1-15 wt % hydroxypropyl cellulose HF, pH adjusted between 4-7. Without limiting in scope exemplary formulations in this range is illustrated in examples.

The invention further provides yet another exemplary formulation of the invention comprising about 0.1-25 wt % clobazam, 0.5-50 wt % dimethylsulfoxide, 0.5-50 wt % Hexylene Glycol, 0.5-50 wt % highly purified diethylene glycol monoethyl ether, 0.5-50 wt % Triacetine, 0.1-20 wt % Lactic acid, 0.5-50 wt %, dimethyl isosorbide, 0.5-30 wt % Caprylocaproyl polyoxyl-8 glycerides, 0.5-50 wt % fatty acid, 0.5-50% wt water, 0.1-30% wt polyvinyl pyrrolidone, 0.1-15 wt % hydroxypropyl cellulose HF, pH adjusted between 4-7.

The invention further provides yet another exemplary formulation of the invention comprising about 0.1-25 wt % clobazam, 0.5-50 wt % dimethylsulfoxide, 0.5-50 wt % Hexylene Glycol, 0.5-50 wt % highly purified diethylene glycol monoethyl ether, 0.5-50 wt % Triacetine, 0.1-20 wt % Lactic acid, 0.5-50 wt %, dimethyl isosorbide, 0.5-30 wt % Caprylocaproyl polyoxyl-8 glycerides, 0.5-50 wt % fatty acid, 0.5-50% wt water, 0.1-30% wt polyvinyl pyrrolidone, 0.1-15 wt % hydroxypropyl cellulose HF, pH adjusted between 4-7.

The invention further provides yet another exemplary formulation of the invention comprising about 0.1-25 wt % clobazam, 0.5-99 wt % dimethylsulfoxide, 0.5-99 wt % polyethyelene glycol-400, 0.5-99% wt propylene glycol, 0.5-99 wt % Propylene glycol monolaurate type II, 0.5-50% wt water, 0.1-15 wt % hydroxypropyl cellulose HF, pH adjusted between 4-7. Without limiting in scope exemplary formulations in this range is illustrated in examples.

The invention pertains to the transdermal delivery of clobazam for the treatment of epilepsy. Another embodiment pertains to the use of acrylic or silicone pressure sensitive adhesive and/or polymer matrix which do not contain functional groups and which are not cross linked, but are able to absorb or solubilize large amount of clobazam and at the same time provide equal or better adhesion to skin and permeation through human skin. More preferred examples of pressure sensitive adhesive (PSAs), that could be used but not limited to, include those based on pure acrylate monomers as well as acrylate copolymers and terpolymers using for example as the co-monomers vinyl acetate or hydrocarbon copolymers which may also include pacifiers and other pressure sensitive adhesive modifiers. Some examples of these PSAs are Durotak 87-900A, 87-901A, 87-2516, 87-9301, Bio PSA-4202, Bio-PSA 4302, Bio-PSA 4502, Bio PSA-4602 and etc.

Another embodiment of invention is to inhibit crystallization in matrix patches using solubilizer an/or solvents and/or permeability enhancing agents by providing stabilization of the patch through absorption and immobilization of the liquid in the patch. For example of such excipients include but not limited to PVP, PVP/PVA, hydroxypropylcellulose, hydroxyethylcellulose, methyl cellulose, sodium carboxymethyl cellulose, colloidal silica, Xanthan gum, and etc.

Another embodiment is in matrix and/or drug-in-adhesive and/or drug-in-polymer with two kinds of enhancers, volatile and non-volatile. Volatile enhancers are the excipients that have a vapor pressure 0.2 mmHg and higher at 20° C. such as dimethylsulfoxide, dimethylisosorbide, diethylene glycol monoethyl ether and etc., while, the non-volatile enhancers are the liquids that have a vapor pressure less than 0.2 mm Hg at 20° C. such as urea, lauryl lactate and etc. Volatile enhancers are the enhancers that will evaporate during drying process of matrix and/or drug-in-adhesive and/or drug-in-polymer preparation.

In another embodiment of the invention is a formulation comprising about 0.1-99 wt % clobazam, 0.5-99 wt % dimethylsulfoxide, 0.5-99 wt % Triacetine, 0.5-99 wt % highly purified diethylene glycol monoethyl ether, 0.5-99 wt % propylene glycol monoluarate type II, 0.1-99 wt % adhesive. More preferably 0.1-50 wt % clobazam, 0.5-50 wt % dimethylsulfoxide, 0.5-50 wt % Triacetine, 0.5-50 wt % highly purified diethylene glycol monoethyl ether, 0.5-50 wt % propylene glycol monoluarate type II, 0.1-90 wt % adhesive.

The invention will be illustrated in more detail with reference to the following Examples, but it should be understood that the present invention is not deemed to be limited thereto.

EXAMPLES

Example 1

Clobazam is lipophilic in nature with Log P value around 2.1 and has been formulated as a liquid (Formulation 1) and gel (Formulation 2) transdermal dosage form (Table 1). All reported values are in weight/weight percentage (% w/w)

TABLE 1

| Ingredients | Formulation 1 | Formulation 2 |
| --- | --- | --- |
| Clobazam | 1 | 5 |
| Transcutol P | 10 | 10 |
| Labrasol | 10 | — |
| PEG-400 | 10 | 10 |
| PG | 10 | 5 |
| DMSO | 10 | 10 |
| DMI | 10 | 10 |
| DPG | 10 | 10 |
| Lactic Acid | 5 | 5 |
| Oleic Acid | 5 | 5 |
| Water | 5 | 5 |
| PVP K-30 | — | 25 |

An optimal mixture design of experiment was used to select the level of the formulation variables. The optimum composition of a 1-20% w/w clobazam formulation will have dimethylsulfoxide 10%, Dimethyl Isosorbide 10%, Dipropylene Glycol 10%, Polyethylene Glycol-400 10%, Lactic acid 5%, Oleic acid 5%, Caprylocaproyl polyoxyl-8 glycerides 10%, highly purified diethylene glycol monoethyl ether 10%, Water 5%.

TABLE 2

| | Formulation | | | | | | | | | |
| Ingredients | 5 | 6 | 7 | 8 | 9 | 10 | 11 | 12 | 13 | 14 |
| --- | --- | --- | --- | --- | --- | --- | --- | --- | --- | --- |
| Clobazam | 5 | 5 | 5 | 5 | 5 | 5 | 5 | 5 | 5 | 5 |
| Transcutol P | 10 | — | 10 | 10 | 20 | 10 | 10 | 10 | 10 | 10 |
| Labrasol | — | 10 | 10 | 10 | 10 | 10 | 10 | 10 | 10 | 10 |
| PG | 5 | 5 | 5 | 5 | 5 | 5 | 5 | 5 | 5 | 5 |
| DMSO | 10 | 10 | 10 | 10 | 10 | 10 | 10 | 10 | 10 | 10 |
| DMI | 10 | 10 | — | 10 | 10 | 10 | 10 | 10 | 10 | 10 |
| DPG | 10 | 10 | 10 | — | — | — | 10 | 10 | 10 | 10 |
| PEG-400 | — | — | — | — | — | 10 | — | — | — | — |
| Lactic Acid | 5 | 5 | 5 | 5 | 5 | 5 | — | 5 | 5 | — |
| Tween-80 | — | — | — | — | — | — | — | — | 5 | — |
| LG-90 | — | — | — | — | — | — | — | — | — | 5 |
| Oleic Acid | 5 | 5 | 5 | 5 | 5 | 5 | — | 5 | — | — |
| PVP K-30 | 25 | 25 | 25 | 25 | 25 | 25 | 25 | 25 | 25 | 25 |
| Water | 5 | 5 | 5 | 5 | 5 | 5 | 5 | 5 | 5 | 5 |

The gel formulation should contain gelling agent or thickening agent or polymer in the range of about 0.1-30% and the optimum composition of a 1-20% w/w clobazam formulation predicted to have dimethylsulfoxide 10%, Dimethyl Isosorbide 10%, Dipropylene Glycol 10%, Polyethylene Glycol-400 10%, Lactic acid 5%, Oleic acid 5%, Caprylocaproyl polyoxyl-8 glycerides 10%, highly purified diethylene glycol monoethyl ether 10%, Water 5% (Table 1 and FIG. 1). However Table 2 lists other combination that also could produce successful gel formulation in accordance with the present invention.

Other than these components, other solvents known to those skilled in the art suitable for use in the present invention can be used to prepare the liquid formulation, and combination thereof.

Example 2

The effect of gelling agents and their concentration on the permeation of Clobazam through human cadaver skin was evaluated and a characteristic graph is shown in FIG. 2 and Table 3. The optimal desired composition of clobazam gel formulation contains 3% hydroxypropyl cellulose HF (klucel HF). Clobazam gel formulation can be gelled by gelling agents including but not limited to, natural polymers such as natural polymers, polysaccharides and its derivatives such as but not limited to (agar, alginic acid and derivatives, cassia tora gum, collagen, gelatin, gellan gum, guar gum, pectin, potassium or sodium carrageenan, tragacanth, xanthan gum, copal, starch, chitosan, resin etc.), synthetic polymers and its derivatives such as without any limitation to carboxy vinyl polymers or carbomers (carbopol 940, carbopol 934, carbopol 971), polyethylene and its co-polymers etc. clays such as silicate etc. polyvinyl alcohol, polyacrylamide, polyvinyl pyrrolidone homopolymer and polyvinyl pyrrolidone copolymers (PVP, Poloxamer), acrylic acid its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, as well as pressure sensitive adhesive based on silicone, or "hot-melt adhesive". In addition, other than human cadaver skin, clobazam can be evaluated with other artificial membranes including but not limited to cellulose membrane, silicone membranes (polydimethylsiloxane), liposome coated membranes, solid-supported liquid membranes, lecithin organogel membrane and other. Besides the gel formulation of clobazam, other dosage forms including but not limited to ointment, creams, emulsion, liposomes, etc. may be used.

TABLE 3

| Ingredients | Formulation | | | | |
|---|---|---|---|---|---|
| | 4 | 18 | 15 | 32 | 34 |
| Clobazam | 5 | 5 | 5 | 5 | 5 |
| Transcutol P | 12 | 20 | 20 | 20 | 20 |
| Triacetine | — | — | — | 10 | 10 |
| Labrasol | 15 | 10 | 10 | 10 | 10 |
| PEG-400 | 10 | 9 | 9 | 12 | 11 |
| PG | 10 | 5 | 5 | — | — |
| DMSO | 10 | 10 | 10 | 10 | 10 |
| DMI | 10 | 10 | 10 | 10 | 10 |
| DPG | 10 | — | — | — | — |
| Lactic Acid | 5 | 5 | 5 | 5 | 5 |
| Oleic Acid | 5 | | | | |
| LG-90 | — | 5 | 5 | 10 | 10 |
| Water | 5 | 5 | 5 | 5 | 5 |
| Carbopol | 3 | — | — | — | — |
| Klucel HF | — | 2 | 2 | 3 | 4 |
| PVP K-30 | — | — | 14 | — | — |

Example 3

The effect of enhancers or solubilizers on the flux of clobazam through human cadaver skin was evaluated. The desire optimum composition of clobazam gel formulation contained dimethylsulfoxide (DMSO), dimethylisosorbide (DMI), Lactic acid, Tween-20, highly purified diethylene glycol monoethyl ether (Transcutol P), dipropylene glycol, polyethylene glycol-400, propylene glycol (PG), Hexylene Glycol (HG), Lauroglycol-90 (LG-90). Apart from above mentioned enhancers and/or solubilizers, the clobazam transdermal delivery can be influenced by enhancers and/or solubilizers including but not limited water, sulfoxides, and similar chemicals such as but not limited to (dimethylsulfoxide, dimethylacetamide, dimethylformamide, decylmethylsulfoxide, dimethylisosorbide etc.), azone, pyrrolidones such as but not limited to (N-methyl-2-pyrrolidone, 2-pyrrolidone etc.), esters such as but not limited to (Propylene glycol monolaurate, butyl ethanoate, ethyl ethanoate, isopropyl myristate, isopropyl palmitate, methyl ethanoate, decyl oleate, glycerol monooleate, glycerol monolaurate, lauryl laurate etc.), fatty acids such as but not limited to (capric acid, caprylic acid, lauric acid, oleic acid, myristic acid, linoleic acid, stearic acid, palmitic acid etc.), alcohols, fatty alcohols and glycols such as but not limited to (oleyl alcohol, ethanol, dodecanol, propylene glycol, glycerol etc.), ethers such as but not limited to (diethylene glycol monoethyl ether), urea, polyoxyethylene fatty alcohol ethers, polyoxyethylene fatty acid esters, esters of fatty alcohols, esters of long chain fatty acids with methyl, ethyl or isopropyl alcohol, esters of fatty alcohols with acetic acid, lactic acid, as well as oleic acid diethanolamine, essential oils, terpene and terpenoids such as but not limited to (terpineol, limonene, thymol, cineole etc.), surfactant type enhancers (polysorbate 80, polysorbate 20 etc.), liposomes, niosomes, transferomes, ethanosomes, polysorbate such as but not limited to (polysorbate 20, polysorbate 40, polysorbate 60, polysorbate 80 etc.), span such as but not limited to (span 80, span 20 etc.), surfactants such as (anionic, cationic, nonionic and amphoteric), propylene glycol monocaprylate type I, propylene glycol monocaprylate type II, propylene glycol dicaprylate, medium chain triglycerides, propylene glycol monolaurate type II, linoleoyl polyoxyl-6 glycerides, Caprylic glyceride, oleoyl-polyoxyl-6-glycerides, lauroyl polyoxyl-6-glycerides, polyglyceryl-3-dioleate, diethylene glycol monoethyl ether, propylene glycol monolaurate type I etc., cyclodextrins, polyhydric alcohol, especially 1,2-propanediol, butanediol, glycerine, polyethylene glycol (m.w. 200 and higher), Dimethyl Sulfoxide, Dimethyl Isosorbide, tetrahydrofurfuryl alcohol, diethyl tolumide, monoisopropylidene glycerine and others Solubilizers, surfactants, emulsifying agents, dispersing agents and similar compounds or chemicals known to those skilled in the art can be used either alone or in combination thereof.

Example 4

A clobazam containing matrix system can be prepared by dissolving clobazam in durotak adhesives. The matrix formulation can be prepared by weighing required amount of 1-30% w/w clobazam, 10-75% w/w plasticizer and 1-40% w/w enhancer in the container-containing durotak adhesive (10-90% w/w) and mixed to obtain a homogenous mixture. If clobazam is not soluble in the adhesive then acetonitrile can be used to solubilize clobazam in the polymer. The homogenous mixture is then coated on the backing membrane using an elastomer coater to get uniform thickness of the matrix system. Dry the coated matrix system for 24 hrs at 80° F. The matrix formulation can be prepared by polymers including but not limited to natural polymers such as natural polymers, polysaccharides and their derivatives such as but not limited to (agar, alginic acid and derivatives, cassia tora gum, collagen, gelatin, gellan gum, guar gum, pectin, potassium or sodium carrageenan, tragacanth, xanthan gum, copal, starch, chitosan, resin etc.), synthetic polymers and their derivatives such as without any limitation to carboxy vinyl polymers or carbomers (carbopol 940, carbopol 934, carbopol 971), polyethylene and its co-polymers etc. clays such as silicate etc. polyvinyl alcohol, polyacrylamide, polyvinyl pyrrolidone homopolymer and polyvinyl pyrrolidone copolymers (PVP, Poloxamer), acrylic acid and its ester, polyacrylate copolymers, isobutylene, ethylene vinyl acetate copolymers, natural rubbers, synthetic rubbers such as styrene-diene copolymers, styrene-butadiene block copolymers, isoprene block copolymers, acrylonitrile butadiene rubber, butyl rubber or neoprene rubber, as well as pressure sensitive adhesive based on silicone, or "hot-melt adhesive". The crystals in the dried coated matrix patch during the preliminary stability study period were observed by naked eye. The cold flow properties of the polymer adhesive of the present invention are considered acceptable when adhesion of the transdermal patch to the skin of the user remains high throughout the drug delivery period and the adhesive does not extend beyond the boundary of patch.

TABLE 4

| Ingredients | Formulation | | | | |
|---|---|---|---|---|---|
| | PM 14 | PM 19 | PM 20 | PM 21 | PM 22 |
| Clobazam | 10 | 10 | 10 | 10 | 10 |
| Triacetine | 15 | 15 | 15 | 15 | 15 |
| DMSO | 15 | 10 | 15 | 15 | 15 |
| LG-90 | 10 | 10 | 10 | 10 | 10 |
| Oleic Acid | — | 5 | — | — | — |
| Durotak-2516 | 50 | 50 | — | — | — |

TABLE 4-continued

| Ingredients | Formulation | | | | |
|---|---|---|---|---|---|
| | PM 14 | PM 19 | PM 20 | PM 21 | PM 22 |
| Durotak-2194 | — | — | 50 | — | — |
| Durotak-9301 | — | — | — | 50 | — |
| Durotak-2074 | — | — | — | — | 50 |

Example 5

Clobazam formulation produced in following table 5 was applied on New Zeeland Albino rabbit (NZAR) skin for an irritation test. The clobazam transdermal formulation gel was applied on NZAR vertebral in 9.6-cm$^2$ areas with the help of hilltop chamber, which can contain 1.2 gm of specimen for 168 Hrs. The test subject fixed with medical tape to prevent detachment from the NZAR skin. After 168 hrs, the medical tape and the patch were removed with care and the primary skin irritation index of the patch for skin irritation including erythema and edema was determined with the help of expert. Following table 6 was shown irritation score for 3 NZAR. Irritation study was performed at Consumer Product Testing Laboratory facility by independent researcher.

TABLE 5

| Ingredients | Formulation 57 |
|---|---|
| Clobazam | 5 |
| Transcutol P | 20 |
| Triacetine | 10 |
| Labrasol | 5 |
| DMSO | 15 |
| DMI | 10 |
| Hexylene Glycol | 12 |
| Lactic Acid | 5 |
| Lauryl Glycol 90 | 10 |
| Tween-20 | 5 |
| Klucel HF | 3 |
| pH | 5.00 |

TABLE 6

Irritation score (Draize Scoring scale)

| Rabbit ID | Hilltop Chamber No | Erythema/Edema |
|---|---|---|
| 832 | 1 | 2/1 |
| | 2 | 2/1 |
| 835 | 1 | 1/0 |
| | 2 | 0/0 |
| 837 | 1 | 1/0 |
| | 2 | 0/0 |

REFERENCES

1. Saleh T. A., Stephen L., "Lenox gastaut Syndrome, review of the literature and a case report", Head and Face Medicine, 4:9, 2008,
2. Al-Banji M. H., Zabar D. K., and Jan M. M., "Lennox-Gastaut Syndrome Management Update", Neuroscience, 20(3), 2015, 207-212
3. Batchelor H. K., Marriott J. F., "Formulation for Children: Problem and Solutions", British Journal of Clinical Pharmacology, 79(3), 2015, 405-418
4. http://www.accessdata.fda.gov/drugsatfda_docs/label2011/202067s0001bl.pdf
5. US 2013/0281542 A1
6. U.S. Pat. No. 8,609,651 B2
7. WO 2008/115590 A1
8. US 2009/0304801 A1

While the invention has been described in detail and with reference to specific examples thereof, it will be apparent to one skilled in the art that various changes and modifications can be made therein without departing from the spirit and scope thereof.

What is claimed is:

1. A Transdermal drug delivery system (TDDS) for administration of Clobazam to a patient comprising:
   An active substance area or reservoir comprising a pharmaceutical composition comprising:
   About 1 to about 20% Clobazam;
   About 0.5 to about 50% solubilizer and/or surfactant selected from the group consisting of polysorbate, triglycerides and its derivatives, diethylene glycol monoethyl ether, polyethylene glycol, dimethyl isosorbide, Caprylocaproyl polyoxyl-8 glycerides, and combinations thereof;
   About 1 to about 15% permeation enhancing agent selected from the group consisting of pyrrolidones, N-methyl-2-pyrrolidone, 2-pyrrolidone, oleic acid, lactic acid, propylene glycol monolaurate type I, propylene glycol monolaurate type II, propylene glycol, polyethylene glycol, dipropylene glycol, hexylene glycol, glycerine, and combinations thereof;
   About 10 to about 90% polymer and/or adhesive matrix selected from the group consisting of polymers based on acrylic acid and its esters, methylcellulose, ethyl cellulose, carboxymethyl cellulose, Hydroxypropyl cellulose, hydroxypropylmethyl cellulose, mixtures of esters of hydrogenated colophony with cellulose derivatives, pressure sensitive adhesives, and combinations thereof,
   further wherein the TDDS comprises an impermeable backing layer and a detachable protective layer, which optionally has a release membrane,
   wherein the percentage of components are weight to weight of the composition, further wherein the TDDS is capable of being applied to the patient for a time period selected from the group consisting of two days, three days, four days, five days, six days, and seven days, characterized in that during the application period of the TDDS a Draize irritation score of the patient is minimum 0 and maximum 2, wherein the TDDS delivers 1-40 mg/day clobazam through the skin to the blood in a subject, and further wherein the TDDS produces up to 2000 ng/ml plasma concentration,
   additionally, wherein the TDDS has an active substance area or reservoir composition weight is about 100 mg/cm2 to about 500 mg/cm2 of active surface area.

2. The TDDS according to claim 1, wherein the active substance area or reservoir is configured as a polymer matrix system, solid dispersion adhesive matrix system, multiple layer adhesive matrix or suspension adhesive matrix or emulsion adhesive matrix system, or a drug-in-adhesive system.

3. The TDDS according to claim 1, wherein the active substance reservoir is constructed in a pouch-shaped system.

4. The TDDS of claim 1, wherein the active substance reservoir is a preparation selected from the group consisting of flowable, viscous, semi-solid, suspension, emulsion and adhesive matrix, solid dispersion, microemulsion, nanoemulsion, nanosuspension, micro suspension and solid solution.

5. The TDDS of claim 1, wherein the active substance reservoir is confined on the skin facing side by an active substance permeable membrane and on the opposite side form the skin by an active substance impermeable layer.

6. The TDDS of claim 1, further comprising an active substance permeable membrane which modifies or controls the rate of active substance release.

7. The TDDS of claim 1, characterized in that the clobazam containing area is a single-, double- or multilayered active substance matrix.

8. The TDDS of claim 1 further comprising an adhesive so that it may be applied as a plaster or bandage.

9. The TDDS of claim 1 wherein the active substance reservoir contains a fiber material, a woven fabric or a nonwoven, to which the active substance is absorbed.

10. The TDDS of claim 1 wherein the clobazam is present in the active substance reservoir either in dissolved or suspended state.

11. The TDDS of claim 1, wherein the TDDS is a drug-in-adhesive composition, further wherein the drug-in-adhesive composition weight is about 5 mg/cm2 to about 30 mg/cm2 and composition weight for pressure sensitive adhesive is about 10% to about 90% of total weight/cm2.

12. A TDDS which is a drug-in-adhesive system for administration of clobazam to a patient, the TDDS comprising:
   An active substance area or reservoir comprising a pharmaceutical composition comprising:
   About 1 to about 30% clobazam;
   About 0.5 to about 50% solubilizer and/or surfactant and/or plasticizer selected from the group consisting of polysorbate, triglycerides and its derivatives, diethylene glycol monoethyl ether, polyethylene glycol, dimethyl isosorbide, Caprylocaproyl polyoxyl-8 glycerides, and combinations thereof;
   About 1 to about 30% permeation enhancing agent selected from the group consisting of pyrrolidones, N-methyl-2-pyrrolidone, 2-pyrrolidone, oleic acid, lactic acid, propylene glycol monolaurate type I, propylene glycol monolaurate type II, propylene glycol, polyethylene glycol, dipropylene glycol, hexylene glycol, glycerine, and combinations thereof;
   About 10% to about 90% pressure sensitive adhesive and/or polymers selected from the group consisting of polymers based on acrylic acid and its esters, methylcellulose, ethyl cellulose, carboxymethyl cellulose, Hydroxypropyl cellulose, hydroxypropylmethyl cellulose, mixtures of esters of hydrogenated colophony with cellulose derivatives, pressure sensitive adhesives, and combinations thereof,
   further wherein the TDDS is a pressure sensitive adhesive system comprising an impermeable backing layer and a detachable release liner,
   wherein the percentage of components are weight to weight of the formulation, further wherein the TDDS is applied for a time period selected from the group consisting of two days, three days, four days, five days, six days, and seven days, characterized in that during the application period of the TDDS a Draize irritation score of the patient is minimum 0 and maximum 2.

13. The TDDS according to claim 3, wherein the pouch-shaped system comprises inner and outer surfaces,
   and the pharmaceutical composition inside the pouch, the pharmaceutical composition comprising:
   About 1 to about 20% clobazam;
   About 0.5 to about 50% solubilizer and/or surfactant selected from the group consisting of polysorbate, triglycerides and its derivatives, diethylene glycol monoethyl ether, polyethylene glycol, dimethyl isosorbide, Caprylocaproyl polyoxyl-8 glycerides, and combinations thereof;
   About 1 to about 15% permeation enhancing agent selected from the group consisting of pyrrolidones, N-methyl-2-pyrrolidone, 2-pyrrolidone, oleic acid, lactic acid, propylene glycol monolaurate type I, propylene glycol monolaurate type II, propylene glycol, polyethylene glycol, dipropylene glycol, hexylene glycol, glycerine, and combinations thereof;
   About 10 to about 90% polymer and/or adhesive matrix selected from the group consisting of polymers based on acrylic acid and its esters, methylcellulose, ethyl cellulose, carboxymethyl cellulose, Hydroxypropyl cellulose, hydroxypropylmethyl cellulose, mixtures of esters of hydrogenated colophony with cellulose derivatives, pressure sensitive adhesives, and combinations thereof; and
   further comprising about 0.1% to about 30% gelling agent,
   further wherein the TDDS comprises:
   The impermeable backing layer; and
   The releasing membrane, which is covered by detachable protective layer,
   wherein, the percentage of component are weight to weight of the formulation, further wherein the application period of the TDDS is for a time period selected from the group consisting of two days, three days, four days, five days, six days, and seven days, characterized in that during the application period of the TDDS a Draize irritation score of the patient is minimum 0 and maximum 2.

14. A TDDS for administration of clobazam to a patient comprising:
   An active substance area or reservoir comprising a pharmaceutical composition comprising:
   About 1 to about 20% clobazam;
   About 0.5 to about 50% solubilizer and/or surfactant selected from the group consisting of polysorbate, triglycerides and its derivatives, diethylene glycol monoethyl ether, polyethylene glycol, dimethyl isosorbide, Caprylocaproyl polyoxyl-8 glycerides, and combinations thereof;
   About 1 to about 15% permeation enhancing agent selected from the group consisting of pyrrolidones, N-methyl-2-pyrrolidone, 2-pyrrolidone, oleic acid, lactic acid, propylene glycol monolaurate type I, propylene glycol monolaurate type II, propylene glycol, polyethylene glycol, dipropylene glycol, hexylene glycol, glycerine, and combinations thereof;
   About 0.1% to about 30% gelling agent;
   further wherein the TDDS comprises an impermeable backing layer; and
   A releasing membrane, which is covered by detachable protective layer,
   wherein, the percentage of components are weight to weight of the formulation, further
   wherein the TDDS is applied for a time period selected from the group consisting of two days, three days, four days, five days, six days, and seven days, characterized in that during the application period of the TDDS a Draize irritation score of the patient is minimum 0 and maximum 2.

15. The TDDS of claim 14 wherein the solubilizer is hexylene glycol.

16. The TDDS of claim 14 wherein the gelling agent is hydroxypropyl cellulose.

17. A method of treating epilepsy comprising the following steps:
   Selecting a patient in need of such treatment;
   Applying to the skin of the patient the transdermal drug delivery system (TDDS) of claim 1,
   wherein the TDDS is applied for 2 day-, 3 day-, 4 day-, 5 day-, 6 day- and/or 7 days characterized in that during the application period of the TDDS a Draize irritation score of the patient is minimum 0 and maximum 2,
   thereby treating epilepsy in the patient.

18. A method of treating epilepsy comprising the following steps:
   Selecting a patient in need of such treatment;
   Applying to the skin of the patient the transdermal drug delivery system (TDDS) of claim 12;
   wherein the TDDS is applied for 2 day-, 3 day-, 4 day-, 5 day-, 6 day- and/or 7 day characterized in that during the application period of the TDDS a Draize irritation score of the patient is minimum 0 and maximum 2,
   thereby treating epilepsy in the patient.

\* \* \* \* \*